(12) United States Patent
Magnon

(10) Patent No.: US 8,291,918 B2
(45) Date of Patent: Oct. 23, 2012

(54) MECHANICALLY REGULATED VAPORIZATION PIPE

(76) Inventor: Michael Magnon, Jefferson, LA (US)

(*) Notice: Subject to any disclaimer, the term of this patent is extended or adjusted under 35 U.S.C. 154(b) by 0 days.

(21) Appl. No.: 12/312,360

(22) PCT Filed: Nov. 6, 2007

(86) PCT No.: PCT/US2007/023417
§ 371 (c)(1),
(2), (4) Date: May 6, 2009

(87) PCT Pub. No.: WO2008/069883
PCT Pub. Date: Jun. 12, 2008

(65) Prior Publication Data
US 2010/0043809 A1 Feb. 25, 2010

(51) Int. Cl.
*A24F 1/22* (2006.01)
*A24F 47/00* (2006.01)
*A61M 15/06* (2006.01)

(52) U.S. Cl. .................. 131/271; 131/194; 128/202.21

(58) Field of Classification Search .................. 131/273, 131/194, 271; 128/202.21, 203.26
See application file for complete search history.

(56) References Cited

U.S. PATENT DOCUMENTS

| | | | | |
|---|---|---|---|---|
| 2,494,776 A | * | 1/1950 | Moss et al. | 131/361 |
| 2,944,554 A | * | 7/1960 | Marguleas | 131/198.2 |
| 3,528,436 A | | 9/1970 | Stephens | |
| 4,141,369 A | | 2/1979 | Burruss | |
| 4,219,032 A | | 8/1980 | Tabatznik | |
| 4,303,083 A | | 12/1981 | Burruss, Jr. | |
| 4,922,901 A | | 5/1990 | Brooks | |
| 4,947,874 A | | 8/1990 | Brooks | |
| 4,947,875 A | | 8/1990 | Brooks | |
| 5,144,962 A | | 9/1992 | Counts | |
| 5,345,951 A | | 9/1994 | Serrano | |
| 5,538,020 A | | 7/1996 | Farrier | |
| 5,993,748 A | | 11/1999 | Wheeler | |
| 6,095,153 A | | 8/2000 | Kessler | |
| 6,125,853 A | | 10/2000 | Susa | |
| 6,354,301 B2 | | 3/2002 | McCoy | |
| 6,446,426 B1 | | 9/2002 | Sweeney | |
| 6,715,494 B1 | | 4/2004 | McCoy | |
| 6,990,978 B2 | | 1/2006 | Shayan | |
| 7,100,618 B2 | | 9/2006 | Dominguez | |
| 2004/0031495 A1 | | 2/2004 | Steinberg | |
| 2006/0107965 A1 | * | 5/2006 | Marshall | 131/330 |
| 2007/0283972 A1 | * | 12/2007 | Monsees et al. | 131/273 |
| 2008/0149118 A1 | * | 6/2008 | Oglesby et al. | 131/194 |

FOREIGN PATENT DOCUMENTS

WO WO 2006/082571 * 8/2006
* cited by examiner

*Primary Examiner* — Richard Crispino
*Assistant Examiner* — Dionne Walls Mayes
(74) *Attorney, Agent, or Firm* — Scott Maddox; Arthur Dula; Law Office of Art Dula

(57) ABSTRACT

A portable vaporization implement, comprising: a tubular section having a hollow interior, an air intake, and an output orifice; a smoking material chamber that is within said hollow interior and that is in fluid contact with said air intake and said output orifice, and is positioned generally in between said air intake and said output orifice, wherein desired components of a smokable substance may be vaporized; and a purely mechanical means for automatically regulating the amount of heat entering said smoking material chamber, whereby the temperature within said smoking material chamber stays within the vaporization range of said smokable substance, wherein said mechanical means allows unimpeded inhalation by the user.

13 Claims, 12 Drawing Sheets

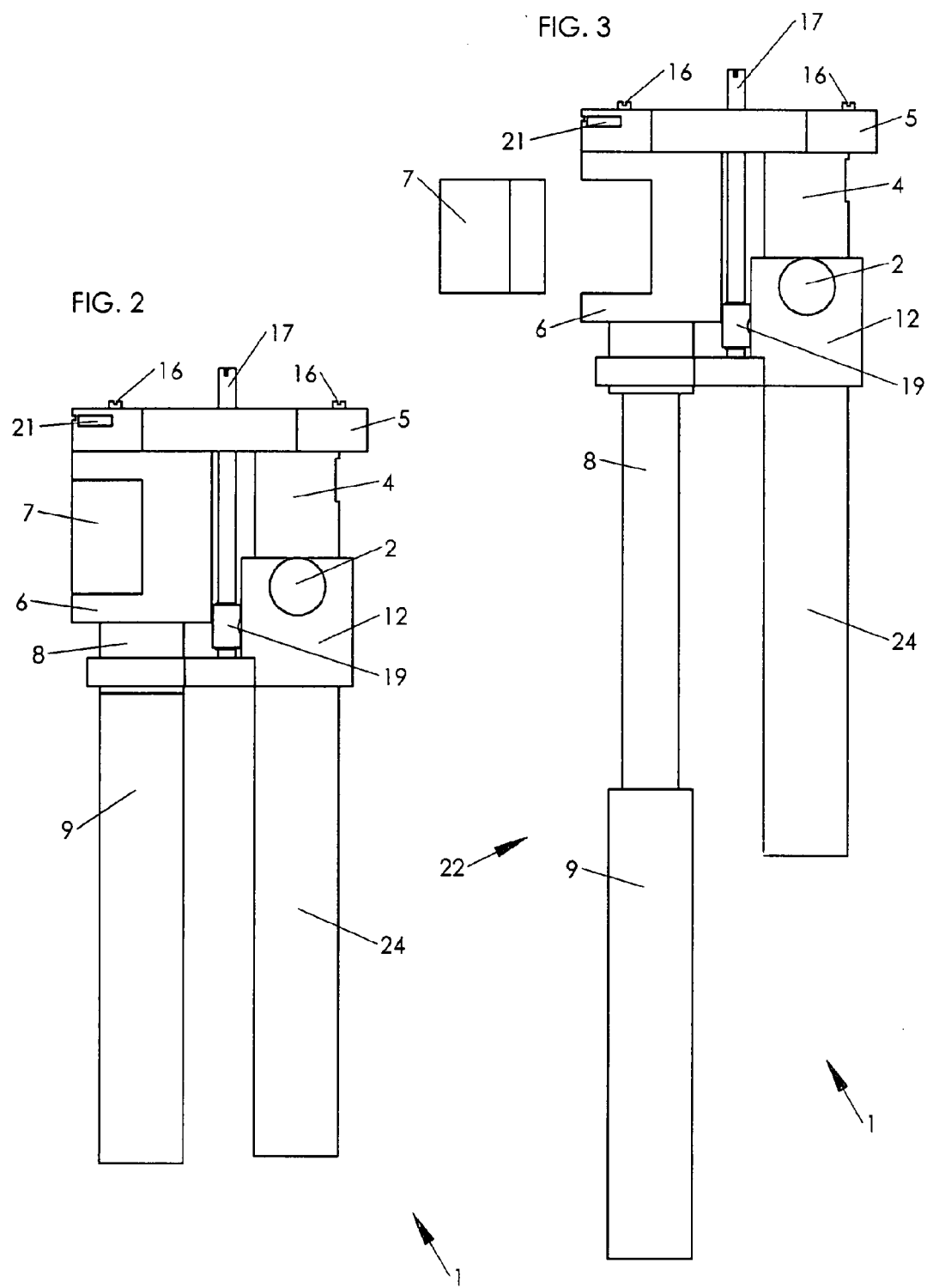

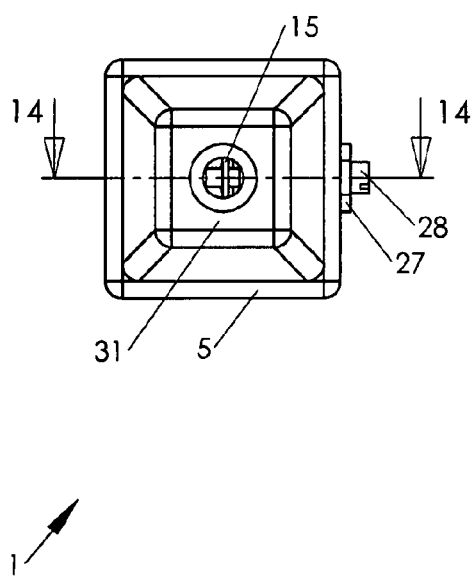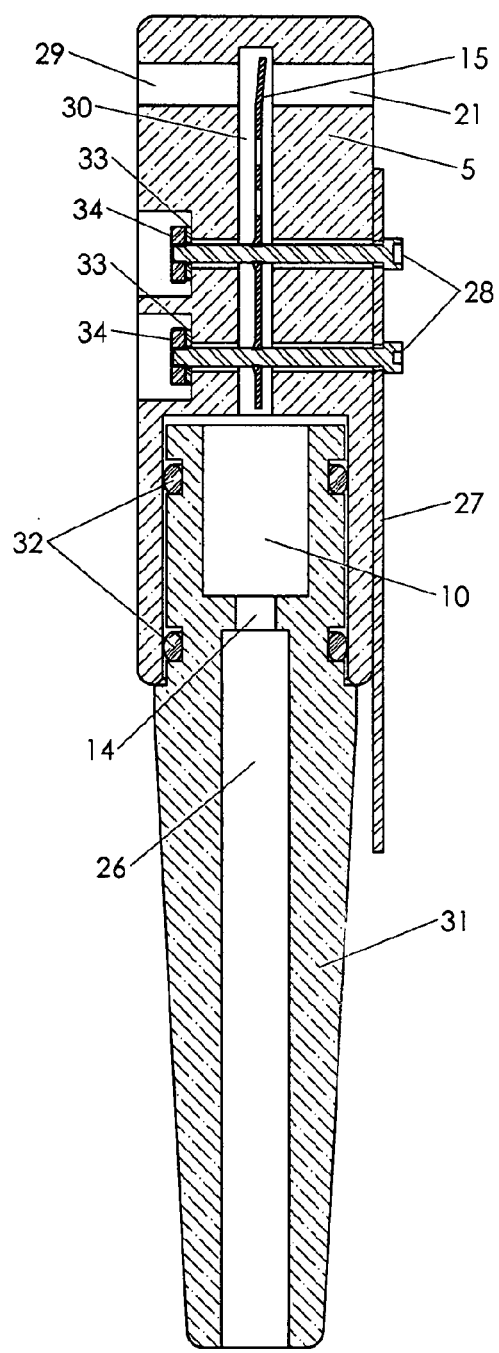

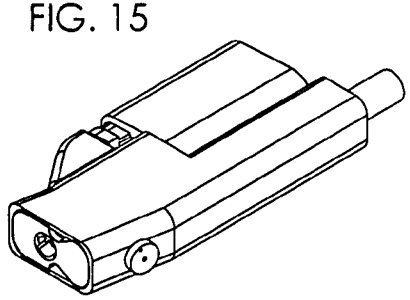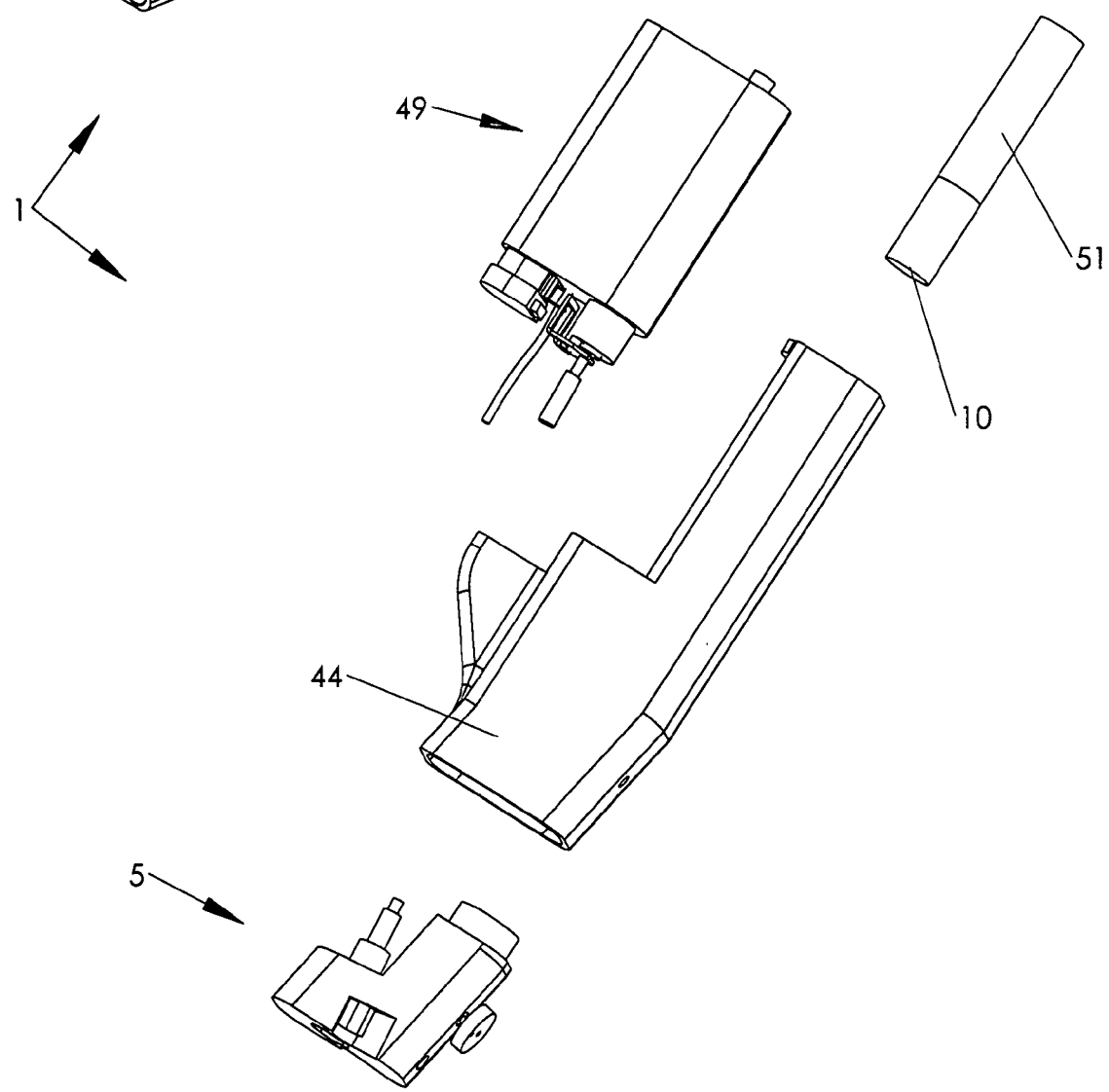

MECHANICALLY REGULATED VAPORIZATION PIPE

FIELD

The present invention relates generally to smoking implements, such as pipes, and more specifically to a vaporization implement, pipe, or the like wherein a mechanical means is provided for maintaining the temperature of the smoking material within its vaporization range by regulating the amount of heat that enters a vaporization chamber that is positioned in between the air intake and the output orifice.

BACKGROUND

Tobacco or other herbs are typically smoked by burning and inhaling the combustion fumes and smoke. Smoking implements are generally known. A common smoking implement is referred to as a pipe. In traditional pipes, tobacco or some other smoking substance is burned, producing smoke for human consumption. Benefits of traditional pipes include simplicity of construction and use, compactness for convenient transport, and low cost.

In recent years, interest has grown in the technique of "vaporization" in which the smoking material is carefully heated so that the desired flavor and psychoactive components are liberated, and combustion is minimized. Vaporization provides many benefits over smoking. When performed properly, vaporization does not produce nearly as much toxic and carcinogenic pyrolytic products as smoking. Also, vaporization is smoother and more flavorful, and lacks a burned taste that many find disagreeable. Further, vaporization allows more efficient use of smoking materials, since psychoactive compounds are not destroyed by combustion. Vaporization occurs at the temperature of the boiling point of the desired active component. Most plants and herbs of interest fall into the temperature range of 220-400 degrees Fahrenheit. A major technical challenge for vaporizers is maintaining the desired temperature range.

Most vaporizers in use today are electrically powered, either directly by electrical line power or indirectly by using a temperature-controlled heat gun.

Electrically/battery powered devices are shown in U.S. Pat. No. 6,990,978; U.S. Pat. No. 5,993,748; U.S. Pat. No. 4,141,369; and U.S. Pat. No. 4,303,083. The most advanced of these devices are capable of adjusting heat output to ensure that the smoking material stays within the desired temperature range. The length of time for heat output is easily controlled. Electrical vaporization devices are not portable and require electrical line power. Some electrical vaporizers are now powered by batteries. Current battery life is less than 30 minutes and the vaporizer is inoperable during recharge. Compared to traditional pipes, electrically powered vaporizers are less rugged, harder to manufacture, less compact and portable and require electrical line power supply or batteries.

U.S. Pat. No. 6,717,494 describes a vaporizer attachment for a pipe so that the pipe can be coupled to an electric heat gun. Carrying the vaporizer attachment with a pipe is only slightly less convenient than carrying a pipe alone, but the added requirement of using an electric heat gun makes this invention less convenient than a traditional pipe. The length of time for heat output is easily controlled. Using an electric heat gun also ensures that an adjustable, consistent temperature heat source is provided, however, no means is provided for adjusting for other variables such as the inhale rate of the smoker or improper placement of the heat source.

U.S. Pat. No. 4,219,032 describes a smoking device using a fuel element, and therefore does not require an electrical/battery powered heat source. The preferred embodiment of this patent requires a liquid reservoir and performance of this embodiment is sensitive to the apparatus' orientation angle from the horizontal. Though an electrical heat source (with the attendant advantages and disadvantages) is within the scope of this invention, the heat source in the preferred embodiment comprises burning charcoal which makes it difficult to precisely control the heat source's start and stop. The preferred embodiment of this invention is not provided with means to automatically adjust the temperature of the smoking materials to ensure that the smoking materials are always hot enough to vaporize the desired components but not hot enough for combustion. No means are provided for adjusting for variables such as the temperature of the burning fuel and the inhale rate of the smoker. This invention requires a separate combustion chamber additional to the bowl which holds the smokable material.

PCT/US2002/041771 discloses a device that uses a flame for vaporizing flavor and psychoactive compounds from smoking materials such as tobacco. Because the preferred embodiment uses butane as a fuel source, it has some of the advantages of traditional pipes. Namely, it requires no electrical power line or batteries. It is relatively more complex and is not as compact and portable as a traditional pipe. The device has a filter unit with a porous flame filter. Flame is supplied to the flame filter, and inhalation causes ambient air to enter the flame filter as well. The flame has to be produced and sustained during each inhalation. The flame exhaust and ambient air are mixed within the flame filter and produce an air stream of intermediate temperature that hopefully is hot enough to vaporize desirable components from the smoking material but not hot enough to burn the smoking material. The temperature of the smoking material will vary with the smokers inhale rate and flame temperature and position. An airflow shutter comprising bimetallic strips is disclosed for making automatic adjustments to maintain the desired temperature of the smoking material by restricting the flow of hot air (making the user's inhalation more difficult) into the vaporization chamber. The disclosed airflow shutter configuration does not permit inhale rates that vary independently of hot air temperature. In other embodiments, maintaining the necessary temperature depends on the skill and experience of the smoker. A bimetallic strip to aid the smoker in determining the temperature near the smoking material is disclosed. The invention requires heat and oxidation resistant flame filters that have high thermal conductivity and are porous enough to breathe through. A flame filter must be designed and sized for the vaporizer. Because the flame filter becomes too hot to safely handle, means for safely attaching/mounting the flame filter must also be provided. Some flame filters require protective coatings. The flame filter ultimately adds complexity, expense, and safety issues not found in traditional pipes.

The present inventor is not aware of any prior art vaporization implement that provides a purely mechanical means for automatically regulating the temperature of a smoking material to vaporize the desired ingredients without burning the smoking material regardless of inhale rate, provides for an effortless inhale, requires no battery or electrical power source, is as conveniently portable, rugged, and easy to use as a traditional pipe, and requires no more additional apparatus than a traditional pipe.

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

SUMMARY

A vaporization implement comprising: a removable vaporization chamber that is within a hollow interior and is in fluid contact with and is positioned generally in between an output orifice and an air intake, wherein desired components of a smokable substance may be vaporized, a temperature sensitive means for mechanically regulating the amount of heat entering said vaporization chamber, an air intake and a hollow interior; when the first and second sections are connected together by joining the first and second connectors; a fueled combustion chamber that is in heat transfer contact with but not fluid contact with the air intake.

BRIEF DESCRIPTION OF THE SEVERAL VIEWS OF THE DRAWINGS

The present invention is illustrated by way of example, and not by way of limitation, in the figures of the accompanying drawings and in which like reference numerals refer to similar elements and in which:

FIG. 2 is a side view of a vaporization implement shown in a collapsed, storage position in accordance with an embodiment of the present invention.

FIG. 3 is a side view of a vaporization implement showing the apparatus in an extended, operating position and with the bowl removed for enabling a user to add a tobacco product to the bowl in accordance with an embodiment of the present invention.

FIG. 13 is an end view of a vaporization implement in accordance with an embodiment of the present invention.

FIG. 14 is a sectional view taken along lines 14-14 of FIG. 13.

FIG. 15 is a perspective view of a vaporization implement in accordance with an embodiment of the present invention.

FIG. 16 is a perspective view of the vaporization implement from FIG. 15 disassembled into four component groups.

DETAILED DESCRIPTION

Figure 1:
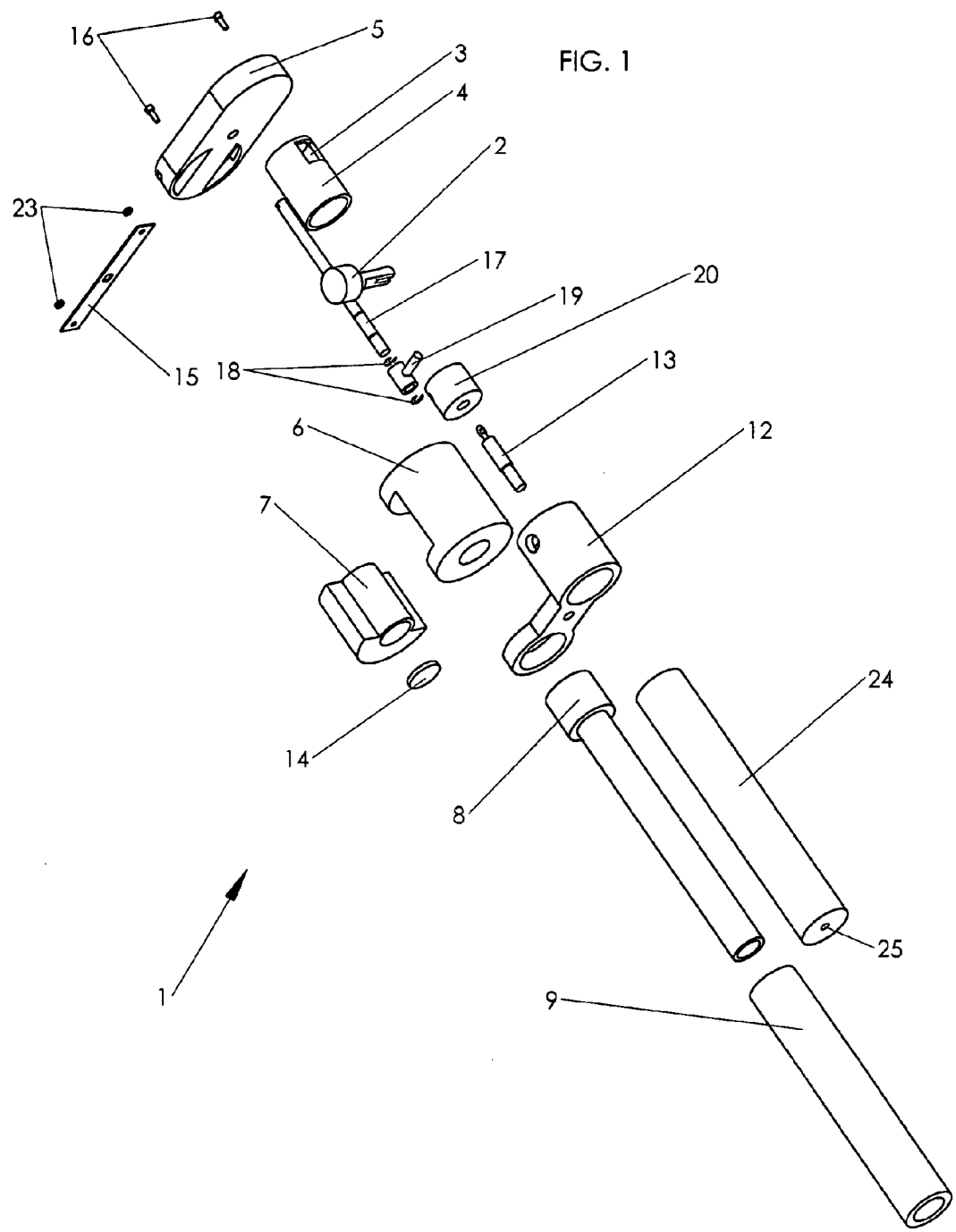
FIG. 1 is an exploded perspective view of a vaporization implement in accordance with an embodiment of the present invention.

In the following description, for the purposes of explanation, numerous specific details are set forth in order to provide a thorough understanding of the present invention. It will be apparent, however, that the present invention may be practiced without these specific details.

An embodiment of the present invention is a vaporizing implement designated generally by 1 in FIGS. 1-9. A fuel container 24 containing a fuel (e.g. butane, propane) is connected to a valve assembly 13 to regulate fuel output. Regulated fuel is combusted in the heat chamber 4 to produce heat. A temperature controlling intake 5 (TCI) is in heat exchange contact with but not fluid contact with the heat chamber 4. An operator is provided with a telescoping mouthpiece 22 that allows air to be inhaled. Inhaled air is heated as it is drawing through the FHAIC 5. Then the heated air is drawn through the smoking material chamber 10. The heated air and vaporized ingredients travel through the telescoping mouthpiece 22 to the operator.

To effectively heat air passing through the TCI 5 internal air paths, the paths have a low cross sectional area to internal surface area ratio. The cross sectional area is preferably small enough to produce a high enough Reynolds number to indicate turbulent flow at the flow rate the operator is inhaling (i.e. typical human inhaling flow rate). Ratios between 0.01 and 0.2 are preferable in the preferred embodiment. The turbulent flow increases convection to ensure that incoming air has ample opportunity for heat transfer interaction with the TCI 5. The heat provided by the combusted fuel transfers into the TCI 5 before being transferred to incoming air. The TCI 5 stores this heat according to its specific heat property and mass to maintain the desired temperature. One means for a low cross sectional area to internal surface area ratio is by providing a maze like air path through the TCI 5.

With the present invention, the chamber 4 is used to heat the TCI 5 through conduction. The TCI 5 temperature is controlled with a manual feedback loop controlling the release of fuel into the heat chamber 4. The TCI 5 has enough thermal capacity to heat the incoming air to the desired temperature with minimal temperature drop itself. This temperature drop causes the release of more fuel. The heat chamber 4 conductively returns the TCI 5 to the correct temperature. The combustion products are exhausted as to not mix with the incoming air.

In FIGS. 1-9, a fuel container 24 is provided, preferably in canister form. Fuel container 24 can contain butane, propane or other fuel source. The fuel container 24 has a valve assembly 13 that can be regulated, enabling a fuel outlet part of the fuel container 24 to be opened or closed. The valve assembly 13 thus enables the flow rate of fuel that escapes from fuel container 24 to be adjusted and the intensity of a flame in heating chamber 4 regulated as to temperature. On the opposite end the fuel container 24 is a fuel fill valve 25 to refill the fuel container 24 with a fuel source.

Heating chamber 4 is coupled to container 24 with bracket 12. The heating chamber 4 provides an ignition window & exhaust vent 3 that enables an operator to ignite the fuel, such as butane or propane that is emitted from container 24 via its valve assembly 13 into heat chamber 4.

Once a flame is applied to ignition window & exhaust vent 3, the fuel is combusted in the heat chamber 4 providing heat. The combustion products are exhausted through the ignition window & exhaust vent 3.

Figure 4:
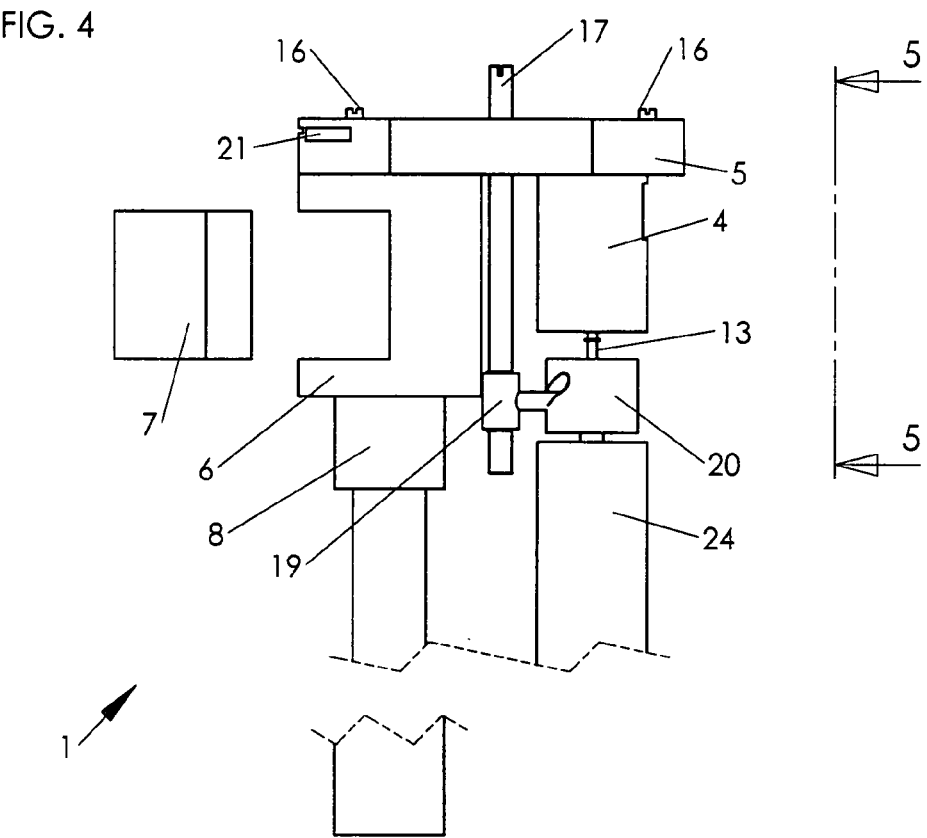
FIG. 4 is a side view of a vaporization implement shown without the bracket and on/off control in accordance with an embodiment of the present invention.
Figure 8:
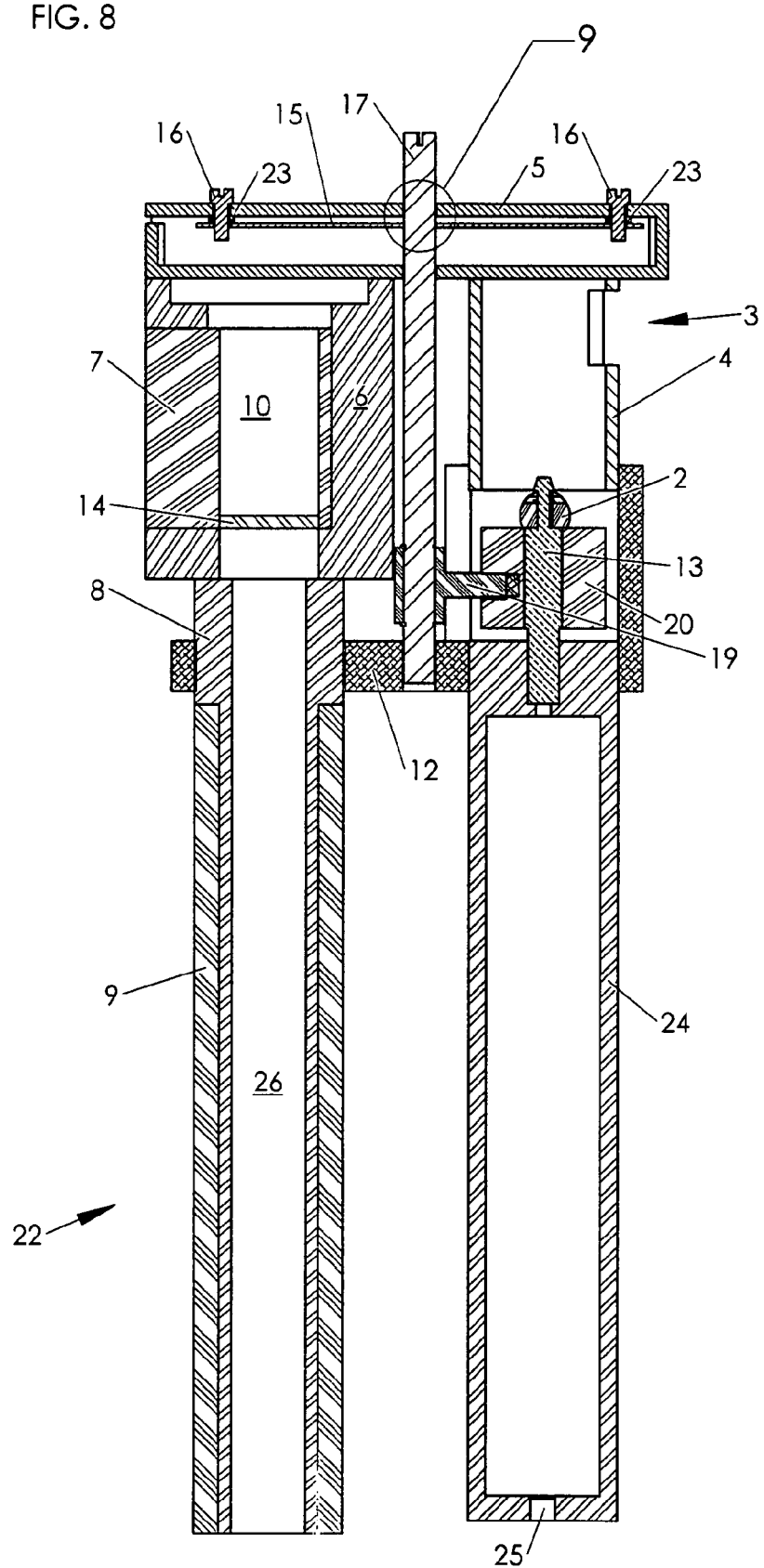
FIG. 8 is a sectional view taken along lines 8-8 of FIG. 6.
Figure 9:
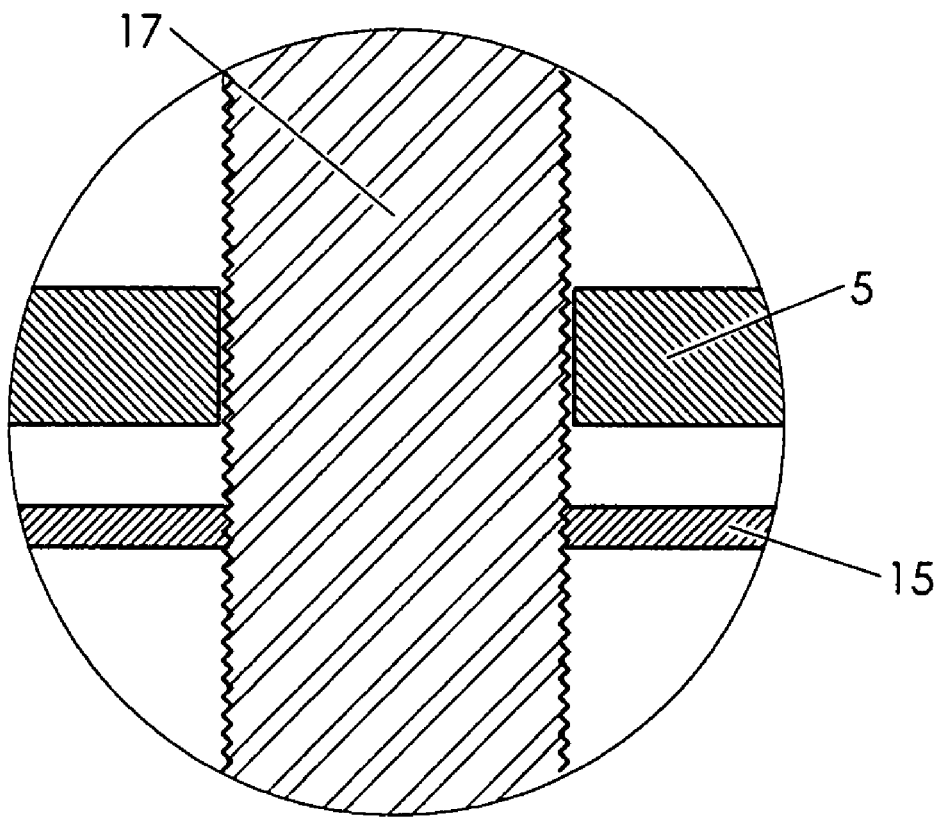
FIG. 9 is a detail view taken from 9 of FIG. 8.
Figure 10:
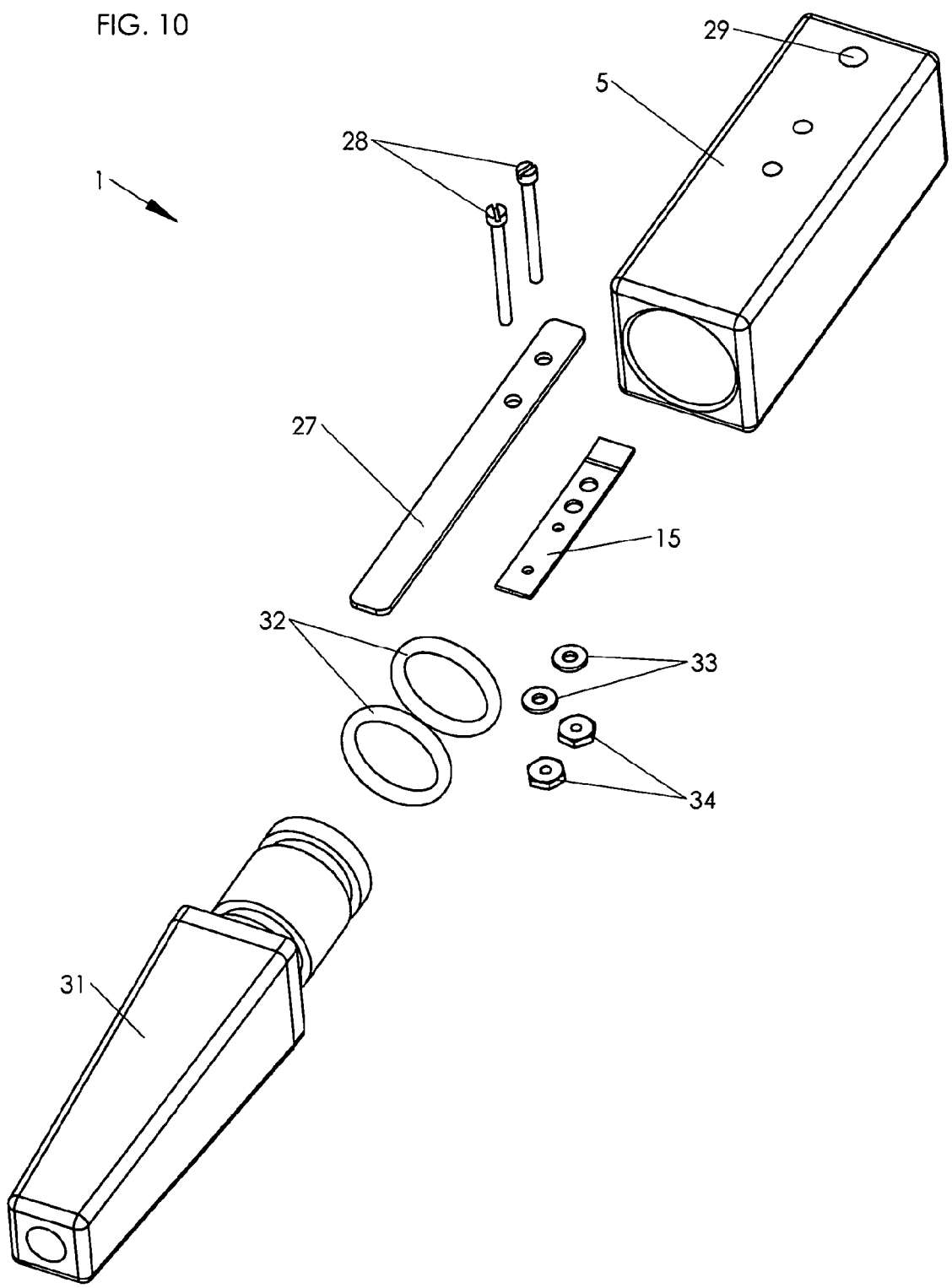
FIG. 10 is an exploded perspective view of a vaporization implement in accordance with an embodiment of the present invention.

TCI 5 is in close thermal communication with heat chamber 4 so that heat transfer takes place between the heat chamber 4 and the TCI 5. FIG. 8 shows the temperature controller 15 is located within the TCI 5. The temperature controller 15 is shown in a simply supported beam configuration held in place with screws 16 and spacers 23, but other configurations are possible to change deflection and/or force as a function of temperature. As the temperature of TCI 5 increases from the fuel burning in heat chamber 4, the temperature of the temperature controller 15 increases. The temperature controller 15 changes position as a function of temperature. The bimetal material used in many thermostats would be a good example of a material to use for the temperature controller 15 and is shown in this embodiment. The control rod 17 is threaded through the temperature controller 15 as shown in FIG. 9 and connects to the valve actuator 19. The thermal deflection of the temperature controller 15 causes axial movement for the control rod 17 and valve actuator 19. Axial motion of the valve actuator 19 causes a rotational motion in the helical slot wheel 20 as shown in FIG. 4. The helical slot wheel 20 is coupled to the valve assembly 13 such that this rotation will open or close the valve assembly 13. The rotation of the valve assembly 13 causes the fuel path to open or close to allow more or less fuel to flow from the fuel container 1. This control circuit will be configured such that an increase in temperature of the TCI 5 and correspondingly the temperature controller 15 will decrease the flow of fuel through the valve assembly 13 and flame intensity in heat chamber 4. This decrease in fuel will stop the increasing temperature in TCI 5 and temperature controller 15, which will cause the temperature controller 15 to stop deflecting. This is how the temperature controller 15 will control the temperature of the TCI 5. This is a feedback device that controls temperature to keep it within a desired range, even under changing conditions (such as variations in inhale rate and ambient temperature), rather than just setting a fixed flame intensity.

The temperature feedback provided by the temperature controller 15 opposes the increasing temperatures and will cause the system to reach a steady state temperature. The steady state temperature is a function of the control rod 17 length measured from the temperature controller 15 to the valve actuator 19. This length determines a relationship between the deflection of temperature controller 15, which is proportional to the temperature of TCI 5 and temperature controller 15, which is proportional to the temperature of TCI 5 and temperature controller 15, and a valve opening position of the valve assembly 13. This length actually determines the steady state temperature. An increase in this length would cause a smaller valve opening for the same temperature, causing the temperature to decrease. This change in temperature causes a change in deflection which causes the valve to open more, but the opening stays smaller with the length change. The net effect is a decrease in the steady state temperature. This length can be changed by the user to select different steady state temperatures by rotating the control rod 17. The control rod 17 is threaded through the temperature controller 15. Each rotation of the control rod 17 changes the temperature controller position by the thread pitch. The position of the valve actuator 19 to the control rod 17 is fixed by using ring clips 18. This method of fixing the valve actuator 19 position axially to the control rod 17 allows for rotation to adjust the effective length of the control rod 17 by adjusting its relative position to the temperature controller 15.

Figure 5:
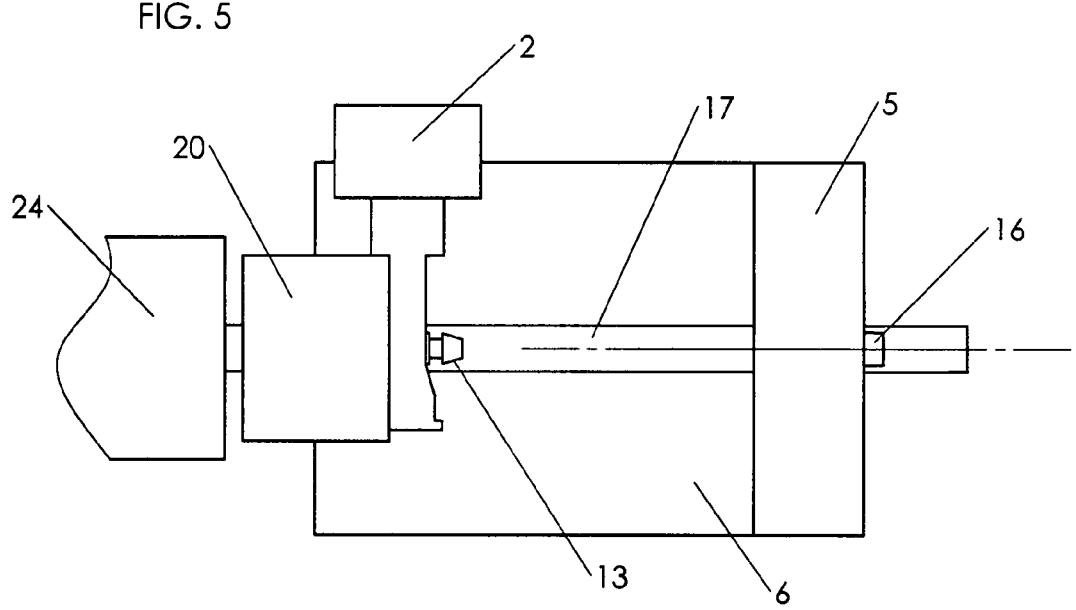
FIG. 5 is a sectional view taken along lines 5-5 of FIG. 4 in accordance with an embodiment of the present invention.

FIG. 5 shows how the on/off control 2 will work. Pulling up on the on/off control 2 will cause the valve assembly 13 to be shifted towards the heat chamber 4. This will lift the valve assembly 13 off its seat and allow the flow of fuel. Butane lighters today work similarly—holding the button down allows the flow of fuel. The on/off mechanism 2 in the valve assembly 13 is independent from the fuel flow control.

Figure 6:
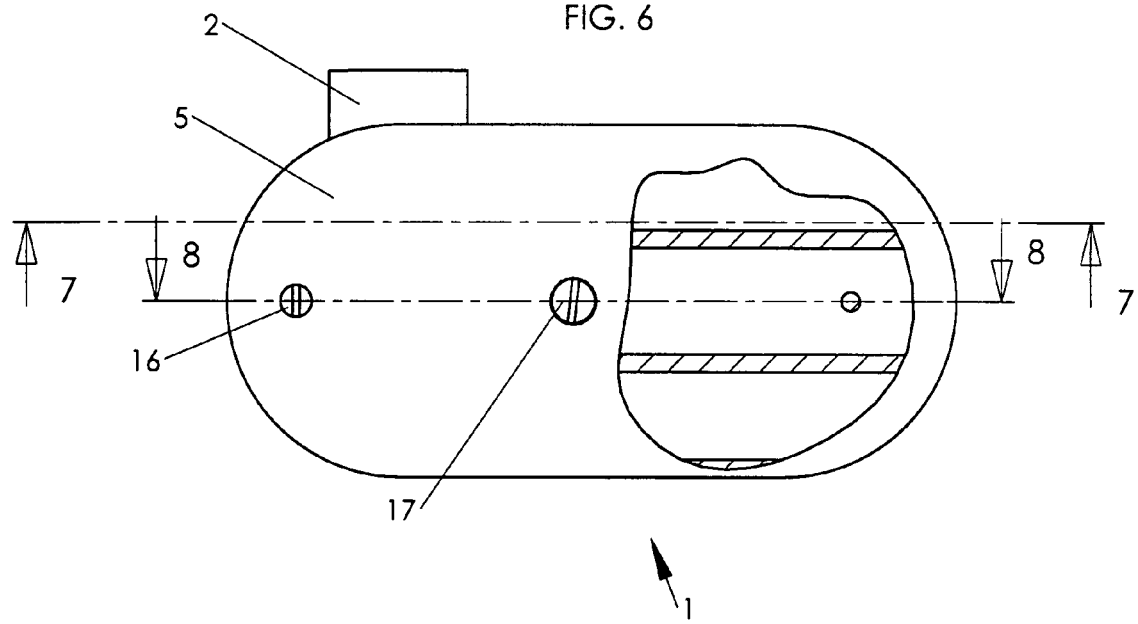
FIG. 6 is an end view of a vaporization implement in accordance with an embodiment of the present invention.
Figure 7:
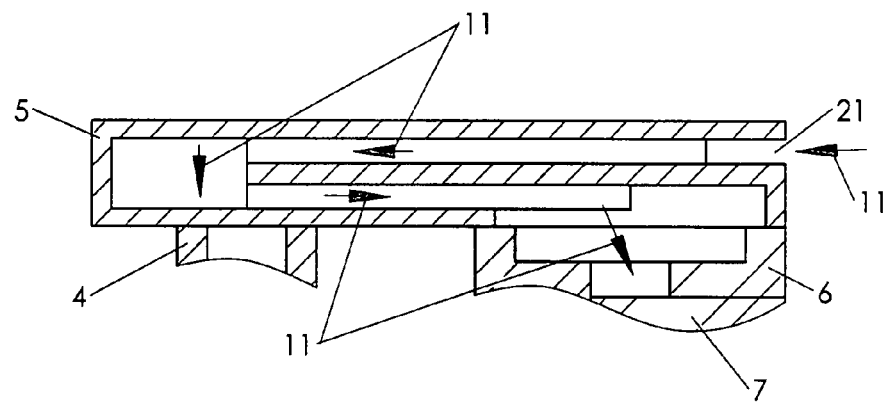
FIG. 7 is a sectional view taken along lines 7-7 of FIG. 6.

FIGS. 6 and 7 illustrate TCI 5 in more detail. It can be seen that the TCI 5 provides a circuitous path for air that enters at ambient air intake port 21, and tracks the path shown by air flow path 11 (arrows) in FIG. 7. Vaporization temperature air travels from TCI 5 to smoking material chamber 10. The smoking material chamber 10 comprises the removable bowl 7 and the screen/filter 14, as shown in FIG. 8. This provides an easy way for consumed smoking material to be replaced with fresh. The removable bowl 7 is placed in the bowl receiver 6 as shown in FIGS. 2 and 3. Heated air traveling through the smoking material chamber 10 vaporizes the desired ingredients in the smoking material and the combination of the two travels through the telescoping mouthpiece 22 to the operator.

The telescoping mouthpiece 22 includes inner tube 8 and outer tube 9. An extended position of the telescoping mouthpiece 22 is shown in FIG. 3. A collapsed, storage position of telescoping mouthpiece 22 is shown in FIG. 2.

By adjusting the effective length of the control rod 17, the amount of heat generated within heat chamber 4 can be regulated to create a steady state temperature of the TCI 5. At this steady state temperature, the TCI 5 heats the incoming air such that air traveling through smoking material chamber 10 is hot enough to vaporize the desired ingredients of a smoking material contained therein without burning same.

Figure 11:
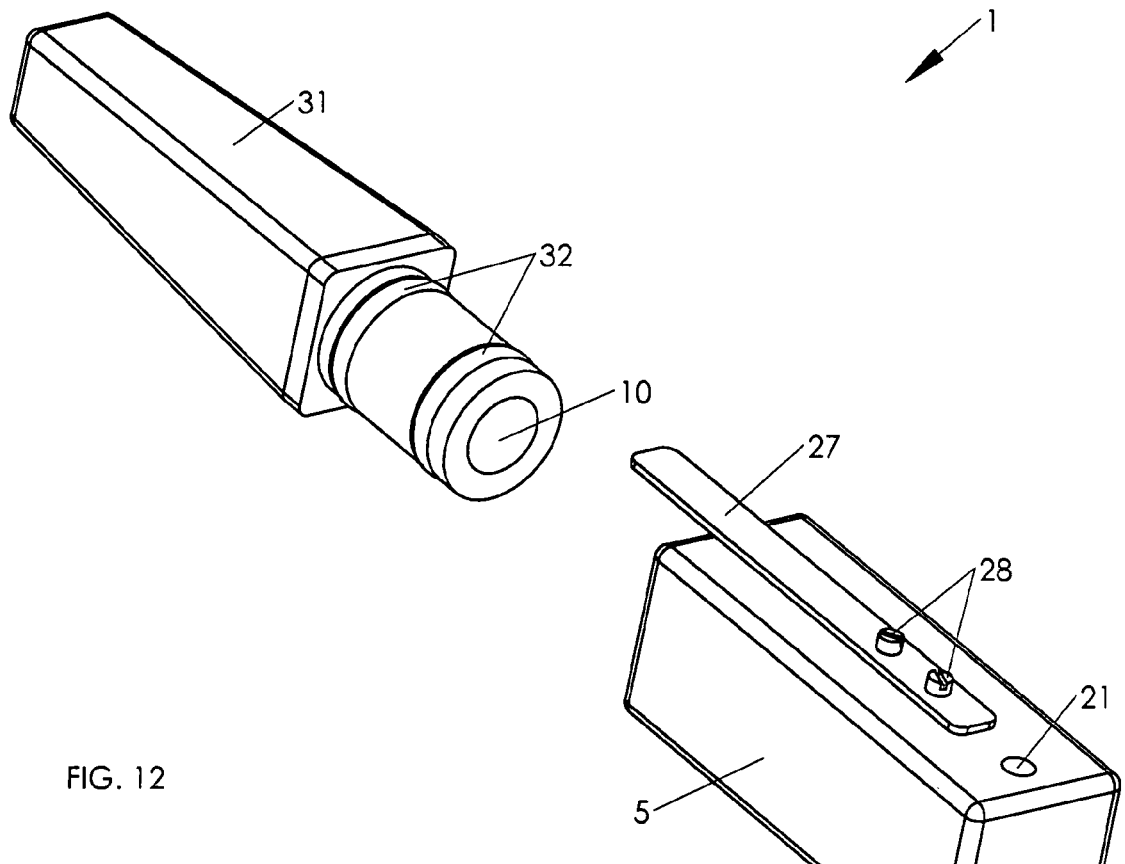
FIG. 11 is a perspective view of a vaporization implement in two separate parts so that tobacco can be inserted into the bowl in accordance with an embodiment of the present invention.
Figure 12:
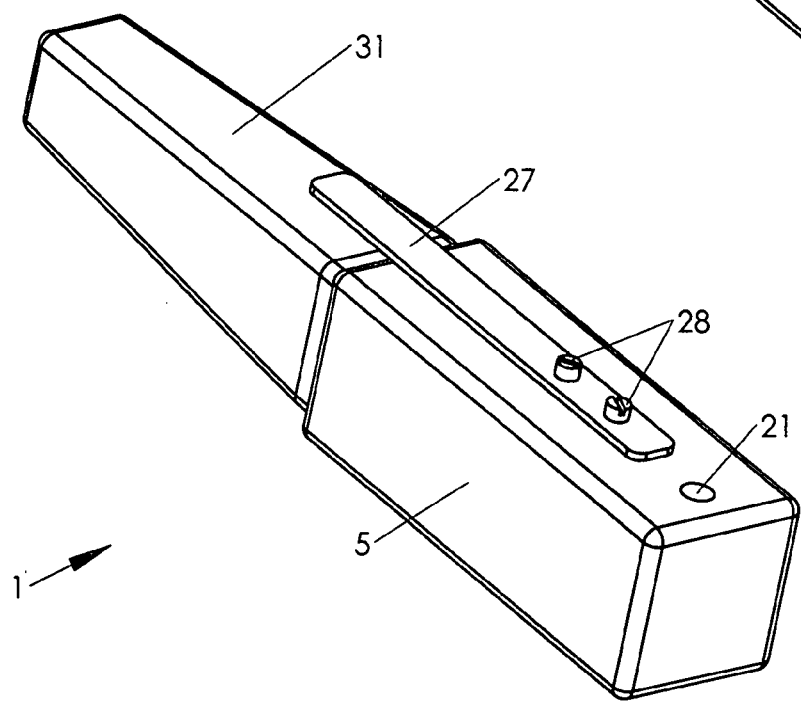
FIG. 12 is a perspective view of a vaporization implement in accordance with an embodiment of the present invention.
Figure 17:
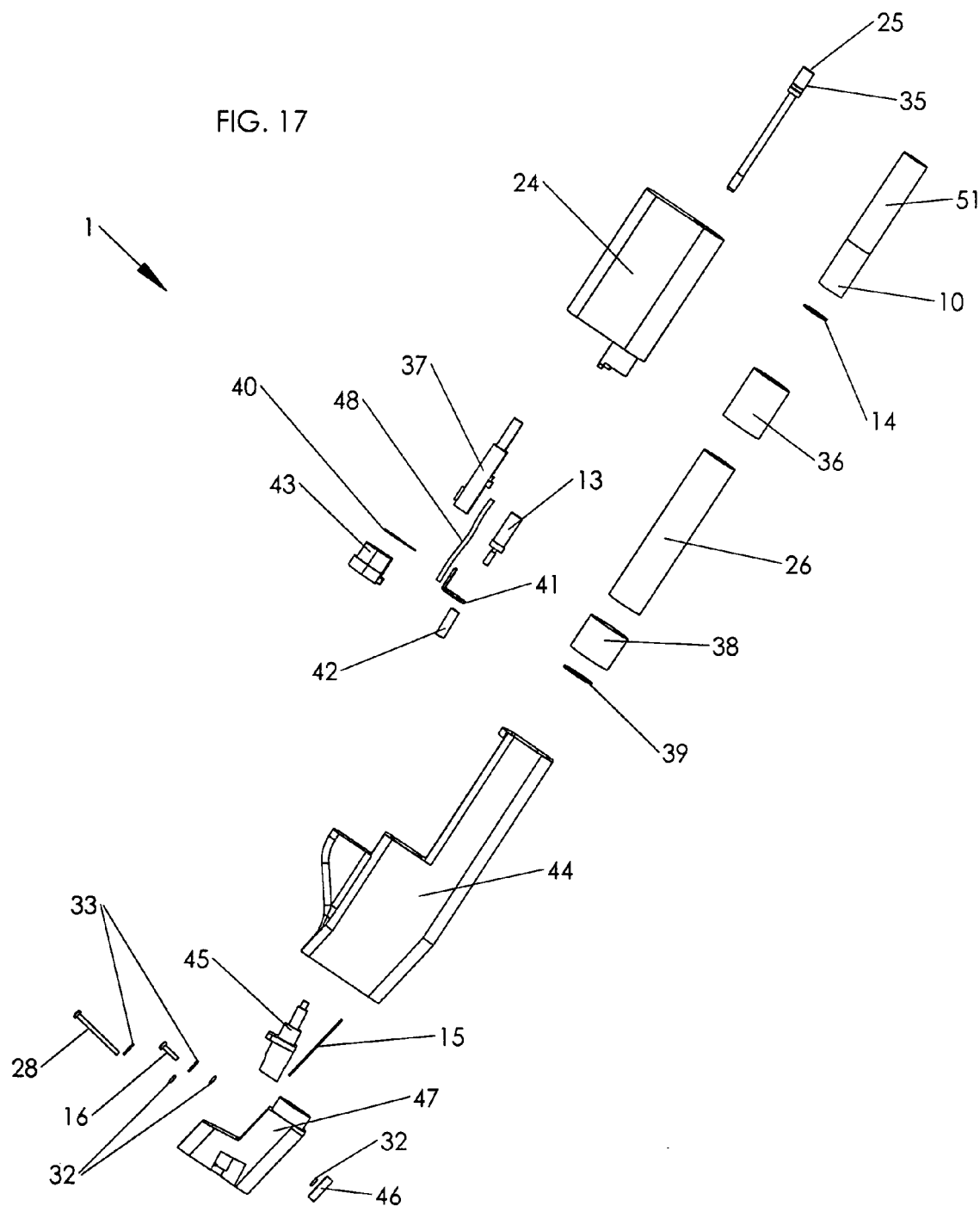
FIG. 17 is an exploded perspective view of the vaporization implement from FIG. 15.

Another embodiment of the present invention is shown in FIGS. 10-14, designated generally by the reference numeral 1. Vaporization implement 1 provides a base/bowl 31 that connects to a temperature controlling intake (TCI) 5. The TCI 5 is a slip fit over base/bowl 31. Two o-rings 32 are provided to create an air tight seal and maintain axial alignment between the TCI 5 and the base/bowl 31. The intake TCI 5 shown in FIG. 12 provides flame intake port 29 and an ambient air intake port 21. Flame intake port and ambient air intake port are in fluid communication with the control chamber 30. Control chamber 30 communicates with smoking material chamber 10. Smoking material chamber 10 communicates with vapor conduit 26 through filter/restriction 14.

In the loading configuration FIG. 11, The TCI 5 is separated from the base/bowl 31. This exposes the smoking material chamber 10 for removal of used smoking material and loading of fresh smoking material. The clip/bowl cleaner 27 designed to facilitate removal of used smoking material if necessary.

In the operating configuration FIG. 12, the TCI 5 is positioned on the base/bowl 31 and o-rings 32 form an air tight seal. As the operator inhales through the vapor conduit 26 contained within the base/bowl 31, air is drawn into the ambient air port 21 and the flame combustion products are drawn into the flame intake port 29. Initially the temperature controller 15 is positioned such that the ambient air intake port 21 is closed, 0% open, and the flame intake port 29 is 100% open. Only flame combustion products can enter the device through the flame intake port. The temperature of the combustion products is very high, for a butane lighter approximately 1800 degrees Fahrenheit. The temperature in the control chamber 30 is determined by the combination of the combustion products and ambient air being mixed. The temperature of the mixed gases traveling through the control chamber 30 convectively heats the temperature controller 15. The temperature controller 15 is made of a temperature sensitive material, possibly bimetal. As the temperature of the temperature controller 15 increases it deflects such that the ambient air intake port 21 opens and the flame intake port 39 closes. As this occurs the temperature of the mixed gases and subsequently the temperature controller 15 decreases. The temperature controller 15 and the control chamber 30 are designed to adjust the openings of these two ports such that the temperature of the mixed gases will quickly reach a steady state temperature. The value of this steady state temperature is controlled by the initial position of the temperature controller 15. This position and consequent steady state temperature is controlled by the two adjustment screws 28. The operator adjusts these adjustment screws 28 to set the desired vaporization temperature.

These temperature controlled mixed gases leave the control chamber 30 and directly enter the smoking material chamber 10. These gases pass through the smoking material and vaporize (boil off) the desired active ingredients without burning the plant material. This vapor passes through the filter/restriction 14, which restrains the smoking material. The vapor passes through the vapor conduit 26 and is inhaled by the operator.

The control chamber 30 is designed such that the operator's inhale rate produces a high enough Reynolds number to cause turbulent flow in the control chamber 30. Turbulent flow increases the heat transfer between mixed gases and the temperature controller 15. This increases the response time of the control system for temperature control.

The temperature controller 15 and the control chamber 30 are designed such that only a small deflection of the temperature controller 15 is necessary to control the steady state temperature. This decreases the control system's sensitivity to the ambient temperature and the combustion products temperature. Low sensitivity to the combustion products temperature means this device will produce a consistent vaporization temperature independent of the flame source. Flame source will need to exceed minimum power required to heat ambient air to the vaporization temperature at the flow rate the operator is inhaling. Excess power will be rejected by the flame intake port. This will allow for any heat source to produce consistent results.

Another embodiment of the present invention is shown in FIGS. 15-20, designated generally by the reference numeral 1. Vaporization implement 1 provides a mouthpiece/bowl 51 which has a slip fit into one end of the vapor conduit 26. This slip fit is sealed air tight by the rear seal 36. The other end of the vapor conduit 26 is joined and sealed air tight to a temperature controlling intake (TCI) 5 using the front seal 38. The front seal 38 also positions the heat diffuser 39 in the flow stream between the TCI 5 and the vapor conduit 26.

Figure 20:
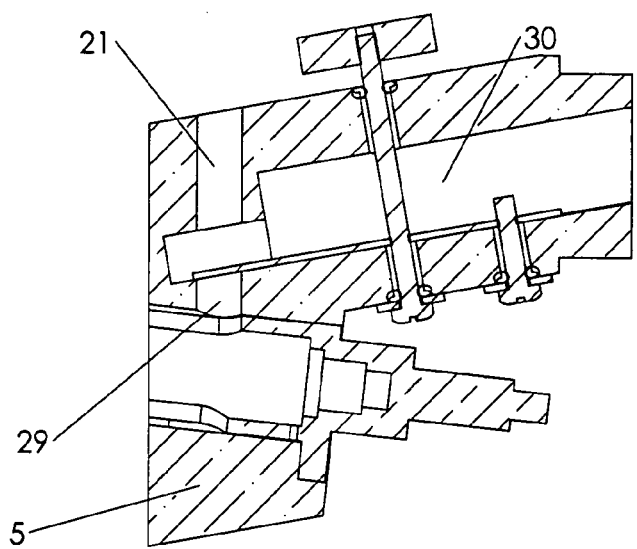
FIG. 20 is a sectional side view of the temperature controlling intake 5 from FIG. 16.

The intake TCI 5 provides flame intake port 29 and an ambient air intake port 21, shown in FIG. 20. Flame intake port and ambient air intake port are in fluid communication with the control chamber 30. Control chamber 30 communicates with vapor conduit 26. Vapor conduit 26 communicates with mouthpiece/bowl 51 through smoking materials chamber 10 then filter/restriction 14.

For the loading configuration, the mouthpiece/bowl 51 is separated from the vapor conduit 26 and rear seal 36 shown in FIG. 16. This exposes the smoking material chamber 10 for removal of used smoking material and loading of fresh smoking material.

In the operating configuration FIG. 15, the mouthpiece/bowl 51 is slipped into the vapor conduit 26 and rear seal 36 to form an air tight seal. Vaporization implement 1 provides an integral heat source 50. The heat source shown is similar to butane lighter. Other fuel gases and different designs could be used. Heat source 50 is comprised of the fuel tank 24, fuel supply valve 13, piezo igniter 37, electrode 40, fuel valve actuator 41, fuel hose 42, button 43, ignition wire 48, fuel fill valve 25, fuel adjustment 35, and torch tip 45. The heat source provides high temperature gases to the flame intake port 29.

Just prior to inhalation the operator presses and holds button 43. The button 43 opens fuel supply valve 13 and causes piezo igniter 37 to discharge high voltage to create a spark in torch tip 45. Spark energy is carried on one side by the electrode 40, fuel valve actuator 41, fuel supply valve 13, fuel hose 42, and torch tip 45, the other side by ignition wire 48. The spark ignites the fuel flowing through the torch tip 45 which produces a steady flame adjacent to flame intake port 29.

As the operator inhales through the mouthpiece/bowl 51, air is drawn into the ambient air port 21 and the flame combustion products are drawn into the flame intake port 29. Initially the temperature controller 15 is positioned such that the ambient air intake port 21 is closed, 0% open, and the flame intake port 29 is 100% open. Only flame combustion products can enter the device through the flame intake port. The temperature of the combustion products is very high, for a butane torch approximately 2100 degrees Fahrenheit. The temperature in the control chamber 30 is determined by the combination of the combustion products and ambient air being mixed. The temperature of the mixed gases traveling through the control chamber 30 convectively heats the temperature controller 15. The temperature controller 15 is made of a temperature sensitive material, possibly bimetal. As the temperature of the temperature controller 15 increases it deflects such that the ambient air intake port 21 opens and the flame intake port 39 closes. As this occurs the temperature of the mixed gases and subsequently the temperature controller 15 decreases. The temperature controller 15 and the control chamber 30 are designed to adjust the openings of these two ports such that the temperature of the mixed gases will quickly reach a steady state temperature. The value of this steady state temperature is controlled by the initial position of the temperature controller 15. This position and consequent steady state temperature is controlled by the temperature adjustment knob 46. The operator adjusts the temperature adjustment knob 46 to set the desired vaporization temperature.

As these temperature-controlled mixed gases leave the control chamber 30 and enter the vapor conduit 26 and smoking material chamber 10, they pass through the heat diffuser 39. The gases may not have mixed enough to be a homogeneous temperature, resulting in some hot and/or cold areas in the flow stream. Hot spots can burn instead of vaporize the smoking materials. The heat diffuser 39 redistributes the heat evenly across the flow stream by using a material with high thermal conductivity in a configuration which thermally couples with the flowing gases, such as a mesh or screen. The gases now have a more uniform temperature profile across the flow stream. These gases pass through the smoking material and vaporize (boil off) the desired active ingredients without burning the plant material. This vapor passes through the filter/restriction 14, which restrains the smoking material. The vapor passes through the mouthpiece/bowl 51 and is inhaled by the operator.

The control chamber 30 is designed such that the operator's inhale rate produces a high enough Reynolds number to cause turbulent flow in the control chamber 30. Turbulent flow increases the heat transfer between mixed gases and the temperature controller 15. This increases the response time of the control system for temperature control.

The temperature controller 15 and the control chamber 30 are designed such that only a small deflection of the temperature controller 15 is necessary to control the steady state temperature. This decreases the control system's sensitivity to the ambient temperature and the combustion products temperature. Low sensitivity to the combustion products temperature means this device will produce a consistent vaporization temperature independent of the flame source and ambient temperatures. Fuel adjustment 35 adjusts the fuel flow rate to the torch tip 45. The fuel flow rate establishes the power available (energy/time). The fuel flow rate power needs to be set higher than the minimum power required to heat ambient air to the vaporization temperature at the inhale rate of the operator. Energy is what changes the temperature of air. Keeping up with the inhale rate of the operator, makes it a power requirement. Excess power will bypass the flame intake port 29 similar to operating the torch without inhaling.

Most excess power exhaust from the torch tip 45 in the form of heat which allows this embodiment to also function as a lighter. Some of the power gets absorbed into the TCI 5. This causes an increase in temperature of the TCI 5 and parts of the case 44. This embodiment provides inductive cooling for the back face of the torch tip 45, largest heat source. The flame in the torch tip 45 gets to 2100 degrees F. To reduce the heat transmitted to the TCI 5 from the back face, the torch tip 45 has an opening opposite from the opening it has for the flame intake port 29. This opening is connected to internal passages in the TCI 5 that circulate pass the back face of the torch tip 45 then connect to openings to the external environment.

Figure 18:
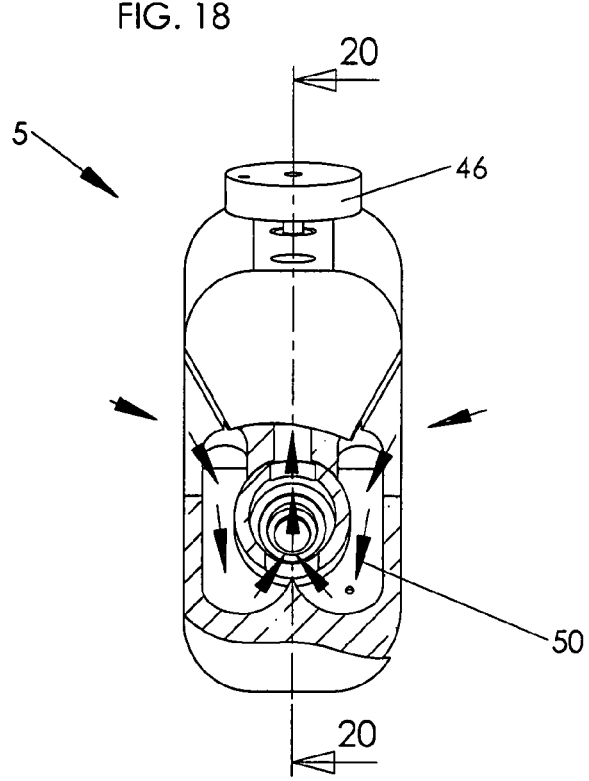
FIG. 18 is an end view of the temperature controlling intake 5 from FIG. 16.
Figure 19:
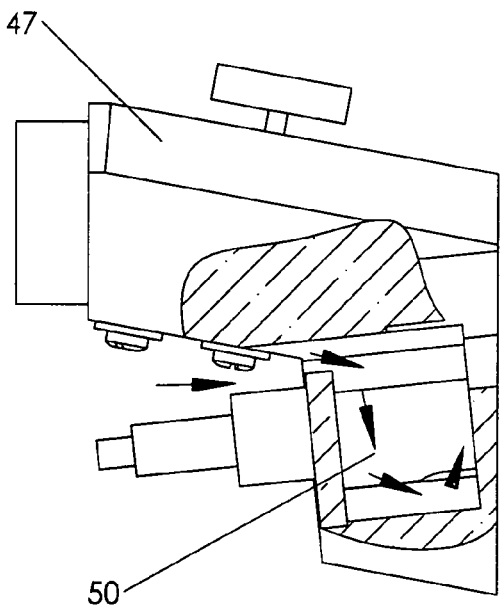
FIG. 19 is an side cutaway view of the temperature controlling intake 5 from FIG. 16.

During inhalation gases are inducted into the flame intake port 29 through the opening in the torch tip 45. These gases are made from combusted fuel, air inducted from the torch tips external opening, and air inducted through the cooling passages. Cooling flow 50 is shown in FIGS. 18 and 19. The air inducted through the cooling passages gets preheated before it is heated by the flame.

All measurements disclosed herein are at standard temperature and pressure, at sea level on Earth, unless indicated otherwise. All materials used or intended to be used in a human being are biocompatible, unless indicated otherwise in the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

I claim:

1. A vaporization implement, comprising:
   a) a first section comprising an output orifice, a hollow interior and a first connector opposite said output orifice;
   b) a second section comprising:
   a control chamber,
   an air intake through which ambient air enters and travels an ambient air path to said control chamber whereby said control chamber is in fluid communication with ambient air,
   a hot gas path whereby hot gas travels to and enters said control chamber and whereby said control chamber is in fluid communication with hot gas,
   and a second connector that is configured to form a connection with said first connector;
   c) wherein said first and second sections provide a vaporization chamber that is positioned generally in between said output orifice and said air intake when said first and second sections are connected together by joining said first and second connectors and said air intake is in fluid communication with said vaporization chamber and said vaporization chamber is in fluid communication with said output orifice; and
   d) wherein said control chamber further comprises a temperature sensing element mounted thereon wherein said temperature sensing element changes its displacement with temperature to regulate the ratio of hot gas to ambient air passing through said control chamber into said vaporization chamber.

2. The vaporization implement of claim 1 wherein said hot gas path or ambient air path of said second section has a cross sectional area that is small enough to cause turbulent flow when an operator inhales on said output orifice.

3. The vaporization implement of claim 1 further comprising a heat chamber mounted on said second section wherein said heat chamber is fueled with a gaseous fuel product to produce hot gas that passes through said hot gas path to said control chamber.

4. The vaporization implement of claim 3 wherein said output orifice defines a tube having a mouthpiece and said tube is telescoping.

5. The vaporization implement of claim 1 further comprising an energy diffuser/screen filter contained within said vaporization chamber.

6. A vaporization implement, comprising:
   a) a vapor conduit that carries vaporized smokeable material components to an operator who inhales;
   b) a smokeable material chamber in which components of a smokeable material are vaporized; and
   c) a temperature controlling intake comprising an ambient air intake port providing fluid communication with ambient air to said temperature controlling intake via an ambient air path, and said temperature controlling intake further comprises a hot gas intake port that is in fluid communication with a supply of hot gas via a hot gas path;
   d) wherein said temperature controlling intake is in fluid communication with said smokeable material chamber and said smokeable material chamber is in fluid communication with said vapor conduit; and
   e) wherein said temperature controlling intake comprises a temperature controller that changes its displacement with temperature and is mounted adjacent to one or more intake ports to at least partially obstruct one flow path as a function of said displacement, and thereby increase the ratio of ambient air to hot gas as vaporization chamber temperature increases above the intended vaporization temperature and to increase the ratio of hot gas to ambient air as vaporization chamber temperature falls below the intended vaporization temperature.

7. The vaporization implement of claim 6 wherein said temperature controller comprises a bimetallic strip.

8. The vaporization implement of claim 6 wherein said vaporization implement portable and small enough to fit easily within a pocket.

9. The vaporization implement of claim 6 wherein:
(a) a first section comprises said temperature controlling intake and a first connector generally opposite said ambient air intake port and said hot gas intake port; and
(b) a second section comprises said smokeable material chamber, a vapor tube, and a second connector configured to form a connection with said first connector, whereby said first section is removably connected to said second section.

10. The vaporization implement of claim 6 wherein said smokeable material chamber comprises a removable bowl.

11. The vaporization implement of claim 6 wherein gas pathways through said temperature controlling intake are narrow enough to make gas flow turbulent.

12. The vaporization implement of claim 6 further comprising a heat chamber in heat transfer contact but not fluid contact with said hot gas path.

13. A vaporization implement, comprising: a) a vapor conduit that carries vaporized smokeable material components to an operator who inhales; b) a smokeable material chamber in which components of a smokeable material are vaporized; and c) a temperature controlling intake having an ambient air intake port; d) wherein said temperature controlling intake is in fluid communication with said smokeable material chamber and said smokeable material chamber is in fluid communication with said vapor conduit; and e) wherein said temperature controlling intake comprises a temperature controller that changes its displacement with temperature; and further comprising: (f) a heat chamber in heat transfer contact but not fluid contact with said temperature controlling intake, (g) a fuel canister and a mechanical linkage between said temperature controller and a valve assembly whereby the flow of a gaseous fuel from said fuel canister into said heat chamber is increased or decreased to regulate the temperature of the gas flow through said temperature controlling intake; and wherein said mechanical linkage comprises a control rod threaded through said temperature controller on one end and having a pin on the other end, wherein said pin engages a helical slot wheel that converts axial motion of said control rod into rotational motion of said helical slot wheel, and wherein said helical slot wheel is mounted on a rotating valve assembly that regulates the flow of fuel into said heat chamber according to said rotational motion.

* * * * *